United States Patent [19]

Spitzer et al.

[11] Patent Number: 4,500,456

[45] Date of Patent: Feb. 19, 1985

[54] PREPARATION OF 4-FLUOROAZETIDINONES USING FClO$_3$

[75] Inventors: Wayne A. Spitzer; Theodore Goodson, Jr., both of Indianapolis, Ind.

[73] Assignee: Eli Lilly and Company, Indianapolis, Ind.

[21] Appl. No.: 453,384

[22] Filed: Dec. 27, 1982

Related U.S. Application Data

[62] Division of Ser. No. 241,989, Mar. 9, 1981, abandoned.

[51] Int. Cl.$^3$ .................. C07D 205/08; C07D 401/04; C07D 403/04; C07B 9/00
[52] U.S. Cl. ............................ 260/239 A; 260/245.4; 260/330.3; 260/330.9; 546/208
[58] Field of Search ............... 260/239 A, 245.4; 546/208

[56] References Cited

U.S. PATENT DOCUMENTS 4,013,653  3/1977  Wolfe .......................... 260/244 R
4,159,984  7/1979  Yoshioka et al. ............... 260/239 A
4,234,724  11/1980  Hashimoto et al. .............. 544/90

OTHER PUBLICATIONS

Spitzer et al., J. Amer. Chem. Soc. 46, 3568 (1981).
Russian Journal of Organic Chemistry.

*Primary Examiner*—Mark L. Berch
*Attorney, Agent, or Firm*—William B. Scanlon; Arthur R. Whale

[57] ABSTRACT

4-Fluoroazetidinone antibacterial agents are provided by a process comprising the reaction of an azetidinone-4-sulfinic acid, or a salt thereof, with perchloryl fluoride (FClO$_3$) at −80° C. to −25° C., e.g., p-nitrobenzyl 3-methyl-2-(2-oxo-4-sulfino-3-phenoxyacetamido-1-azetidinyl)-3-butenoate is reacted with FClO$_3$ to provide corresponding 4-fluoroazetidinone. The latter is isomerized with a tertiary amine to corresponding 2-butenoate which a carboxy group deprotection provides an antibacterial compound.

5 Claims, No Drawings

PREPARATION OF 4-FLUOROAZETIDINONES USING FCLO₃

This application is a division, of application Ser. No. 241,989, filed Mar. 9, 1981 now abandoned.

BACKGROUND OF THE INVENTION

This invention relates to β-lactam compounds. In particular, this invention relates to 4-fluoroazetidinone compounds obtained from penicillins and to a process for the preparation thereof.

The β-lactam antibiotics, the penicillins and the cephalosporins, are well known substances which are generally prepared by semi-synthetic methods. These antibiotics are bicyclic compounds having a 4-membered lactam ring fused to another heterocyclic ring. Recently, however, newer monocyclic β-lactam antibiotics have been developed. Nocardicin, U.S. Pat. No. 3,923,977, is one example of a monocyclic β-lactam antibiotic.

4-chloroazetidinones are used as intermediates in the process described by S. Wolfe, U.S. Pat. Nos. 3,948,927, 3,950,352, 4,013,653, and 4,071,512, in the preparation of the so-called 1-oxapenicillins and the corresponding 1-oxa(dethia)cephalosporins. Further, Narisada *Heterocycles*, Vol. 77, No. 2 (1977), pp. 839–849 reports the preparation of 1-oxa-β-lactam antibiotics with 4-chloroazetidinones.

Since it is known that the four-membered β-lactam ring is a key structural feature of the known β-lactam antibiotics considerable research has been directed to finding new monocyclic β-lactam compounds for use as antibiotics and as intermediates in the preparation of the new β-lactam antibiotics.

SUMMARY OF THE INVENTION

This invention provides 4-fluoroazetidinones represented by the following general formula.

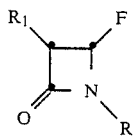
(I)

wherein R₁ is amino or an acylated amino group, and R is a carboxy-substituted butenyl group or an esterified carboxy-substituted butenyl group of the following formulas

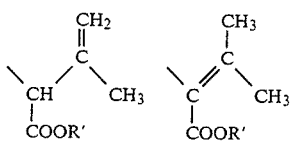

wherein R' is hydrogen or a carboxy protecting group.

The compounds of the invention represented by the formula I wherein R is an acylated amino group are prepared by reacting a 3-acylated-amino azetidinone-4-sulfinic acid with perchloryl fluoride at sub-zero temperatures. The compounds of the above formula, wherein R is an amino group, are prepared by the N-deacylation of an acylamino-4-fluoroazetidinone product of the process.

The 4-fluoroazetidinones of the above formula wherein R is a carboxy- or esterified carboxy-substituted butenyl group having the double bond in the α,β-position are prepared with the corresponding isomer having the double bond in the β, 2-position by isomerization with a tertiary alkylamine.

The 4-fluoroazetidinone compounds of the above formula wherein R₁ is an acylamino group and R is the carboxy-substituted butenyl group having the double bond α,β are antibacterial agents.

DETAILED DESCRIPTION OF THE INVENTION

The compounds provided by this invention are represented by the following structural formula 1.

(1)

wherein R₁ is amino or (1) an imido group of the formula

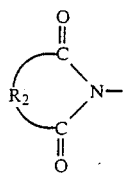

wherein R₂ is C₂–C₄ alkylene or 1,2-phenylene;

(2) an amido group of the formula

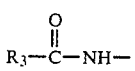

wherein R₃ is (a) hydrogen, C₁–C₄ alkyl, halomethyl, cyanomethyl, benzyloxy, p-nitrobenzyloxy, t-butyloxy, 2,2,2-trichloroethoxy, or p-methoxybenzyloxy;

(b) the group R', wherein R' in phenyl or phenyl substituted by 1 or 2 halogens, hydroxy, protected hydroxy, nitro, cyano, C₁–C₄ alkyl, or C₁–C₄ alkoxy;

(c) a group of the formula

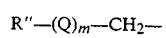

wherein R" is R' as defined above, 1,4-cyclohexadienyl, thienyl or furyl; m is 0 or 1; and Q is O or S; with the limitation that when m is 1, R" is R';

(d) a group of the formula

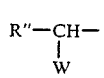

wherein R" is as defined above, and W is hydroxy, protected hydroxy, carboxy, protected carboxy, amino, or protected amino;

(3) an imidazolidinyl group of the formula

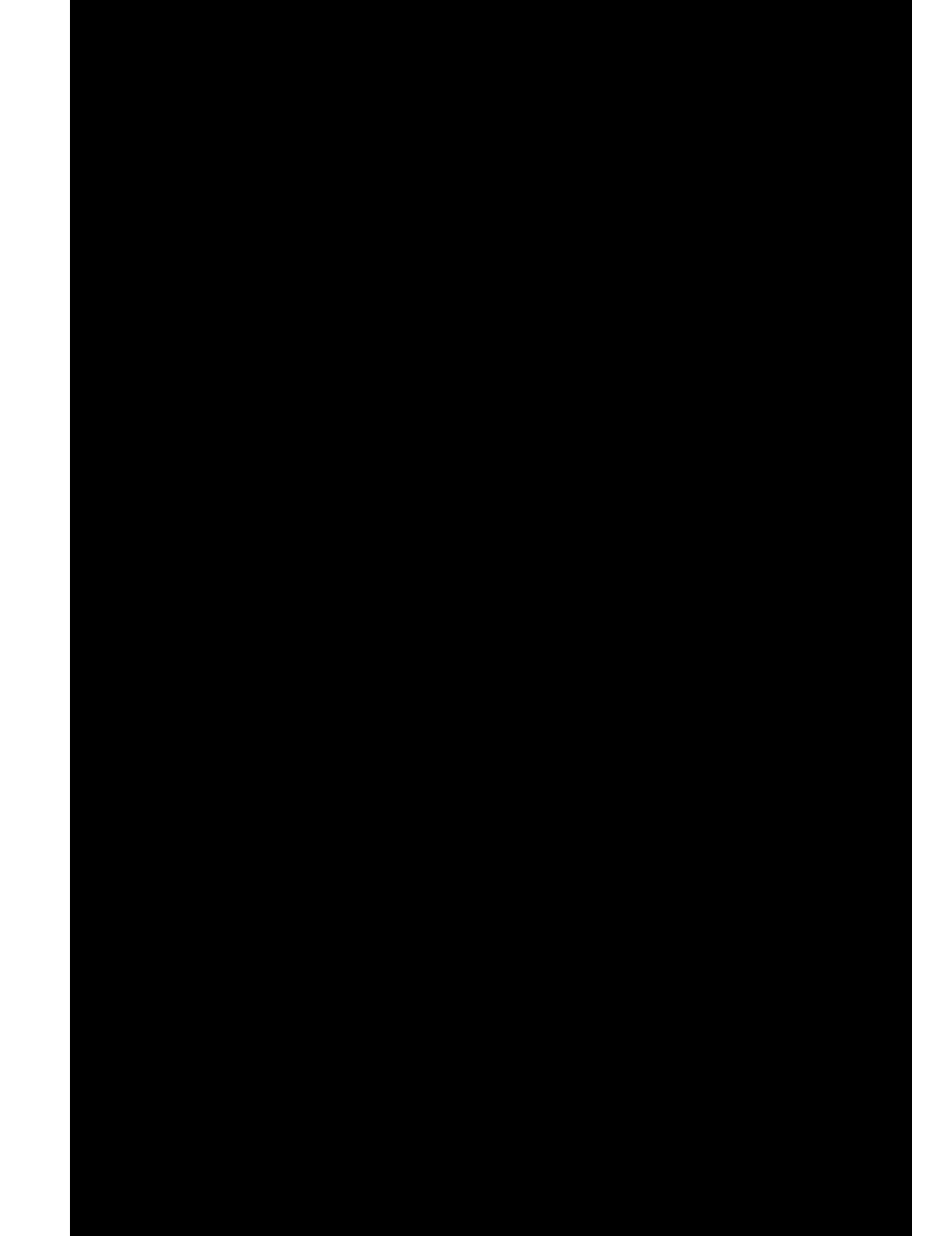

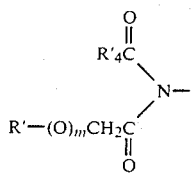

are N-acetyl-N-phenylacetylamino, N-trichloroethoxycarbonyl-N-phenoxyacetylamino, N-propoxycarbonyl-N-(4-chlorophenoxy)acetylamino, N-(2-bromoacetyl)-N-phenoxyacetylamino, and like acyclic imido groups.

Representative of $R_1$ when $R_1$ is an imidazolidinyl group of the formula

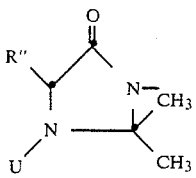

are the 2,2-dimethyl-3-nitroso-5-oxo-4-phenyl-1-imidazolidinyl group, the 2,2-dimethyl-3-nitroso-5-oxo-4-(4-benzyloxyphenyl)-1-imidazolidinyl group, the 2,2-dimethyl-3-acetyl-5-oxo-4-(1,4-cyclohexadien-1-yl)-1-imidazolidinyl group, the 2,2-dimethyl-3-nitroso-5-oxo-4-(2-thienyl)-1-imidazolidinyl group and like substituted imidazolidinyl groups.

The term $R_5$ in the formula 1 represents a conventional carboxy-protecting ester group, for example, those ester groups commonly used to protect carboxylic acid functions in the penicillin and cephalosporin art. Illustrative of such groups are the alkyl and substituted alkyl ester groups such as t-butyl, 2,2,2-trichloroethyl, 2,2,2-tribromoethyl, 2-iodoethyl, phthalimidomethyl, and the like; the arylalkyl groups such as benzyl, p-nitrobenzyl, p-methoxybenzyl, di-phenylmethyl, 4-methoxydiphenylmethyl, methylbenzyl, 3,5-dihydroxybenzyl, and the like. Such esters are employed in this process to prevent the untoward reaction of the carboxylic acid function with the fluorinating reagent.

Examples of amino-protecting groups which can be used in the process to likewise block the free amino function include the conventional amino protecting groups such as those forming urethanes with the amino group eg., t-butyloxycarbonyl, cyclopentyloxycarbonyl, 2,2,2-trichloroethoxycarbonyl, benzyloxycarbonyl, p-nitrobenzyloxycarbonyl, diphenylmethoxycarbonyl, and the like; those forming enamines with β-dicarbonyl compounds eg., methyl acetoacetate and ethyl acetoacetate; and other groups such as the trityl group.

Hydroxy-protecting groups which are conventional and are useful in the process include the halo ester type such as chloroacetyl, trichloroacetyl, dichloroacetyl and bromoacetyl; the ethers such as tetrahydropyranyl, 1-ethoxyethoxy (obtained on protection of the hydroxy group with ethyl vinyl ether), and the like; the silyl groups eg., trialkylsilyl groups such as trimethylsilyl, triethylsilyl, etc.

Other carboxy, amino and hydroxy-protecting groups are well known for example, those described in Chapters 2, 3, and 5, "Protecting Groups In Organic Chemistry", J. F. W. McOmie, Ed., Plenum Press, New York, N.Y. 1973.

The compounds of the invention represented by the formula 1 wherein $R_1$ is a group other than amino are prepared by reacting an azetidinone-4-sulfinic acid or a salt thereof as represented by the following structural formula 2.

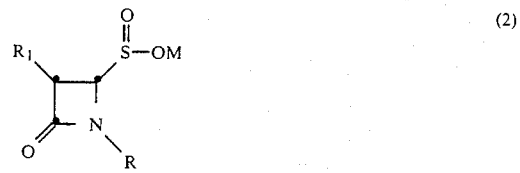

wherein R is a group other than amino as defined above for formula 1, R is as defined above for formula 1, M is hydrogen, sodium or potassium, W is a protected hydroxy, carboxy, or amino group, and $R_5$ is a protected carboxy group; with perchloryl fluoride in an inert aprotic organic solvent at a temperature between about $-80°$ C. and about $-25°$ C.

Perchloryl fluoride, $FClO_3$, is a gas under normal conditions of temperature and pressure having a boiling point of about $-45°$ C. The literature sources which describe the preparation and safe handling of this reagent are Fieser and Fieser, *Reagents for Organic Synthesis*, Vol. 1, page 802, and the bulletin, "Perchloryl Fluoride", Pennsalt Chem. Corp.

Since this reagent is a strong oxidizing agent, the term "inert aprotic solvents" refers to solvents which are non-oxidizable by the reagent under the conditions of the process. Aprotic organic solvents which are useful in the process include, for example, dimethylformamide, dimethylacetamide, acetonitrile, tetrahydrofuran, halogenated hydrocarbon solvents such as methylene chloride and chloroform, and like aprotic solvents.

The reaction is carried out by preparing a solution or suspension of the azetidinone-4-sulfinic acid or a salt thereof in an aprotic solvent, which solution is cooled to the temperature of the process and a solution of perchloryl fluoride in an aprotic solvent such as dimethylformamide is added by dropwise addition with stirring to the solution or suspension. Preferably, the process is carried out by employing one molar equivalent of perchloryl fluoride or a slight excess thereof, for example, 1.1 molar equivalents per mole of the azetidinone-4-sulfinic acid.

Alternatively, the cold solution or suspension of the azetidinone sulfinic acid is treated with gaseous perchloryl fluoride by slowly bubbling the gas into the cold solution with stirring.

The process is illustrated by the following reaction scheme wherein $R_1$ is an acylamido group as defined for formula 1.

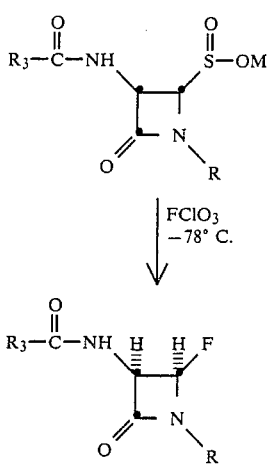

In an example of the process of this invention, p-nitrobenzyl 3-methyl-2-(2-oxo-4-sulfino-3-phenoxyacetamido-1-azetidinyl)-3-butenoate is dissolved in methylene chloride, the solution is cooled to −78° C. in a dry ice-acetone bath and a cold solution of one molar equivalent of perchloryl fluoride in dry dimethylformamide is added by dropwise addition. The reaction proceeds rapidly and is generally complete within 30 minutes.

As shown by the structural formula 1, the cis-fluoroazetidinone is the stereochemical isomer obtained by the process of this invention. The acylamido group or the diacylamido group, $R_1$, has the natural or $\beta$-configuration, while both protons in the 3- and 4-positions of the $\beta$-lactam ring are cis.

The compounds of the formula 1 wherein R is a carboxy-substituted or esterified carboxy-substituted butenyl group having the double bond in the $\alpha,\beta$-position, as shown in the following formula A, are prepared by the isomerization of the corresponding carboxy-substituted or esterified carboxy-substituted butenyl group represented by the formula B.

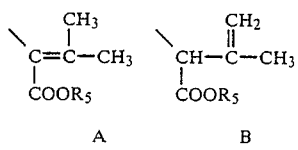

The isomerization is carried out by treating a 4-fluoroazetidinone of the formula 1 wherein R is a butenyl group represented by the above formula B with a tertiary amine such as a trialkylamine, for example, triethylamine, in an inert hydrocarbon solvent such as methylene chloride, dichloroethane, or chloroform. The isomerization can be carried out either on the azetidinone-4-sulfinic acid wherein R is a butenyl group having the double bond in the $\beta,\gamma$-position (formula B), or on the corresponding 4-fluoroazetidinone. Accordingly, an azetidinone-4-sulfinic acid wherein the butenyl group, R, is either isomer can be used in the fluorination process of this invention to provide the corresponding 4-fluoroazetidinone. For example, an azetidinone-4-sulfinic acid represented by the formula 1 wherein R is a butenyl group of the formula B is dissolved in methylene chloride and is treated with 2 molar equivalents of triethylamine. The isomerization product, wherein R is a butenyl group of the formula A, above is recovered from the isomerization mixture by washing the reaction mixture with dilute acid to remove the tertiary amine. After drying the reaction mixture, the solvent is evaporated to provide the isomerization product. When an azetidinone-4-sulfinic acid is employed in the isomerization reaction 2 molar equivalents of the tertiary amine or a slight excess thereof are employed. One molar equivalent is tied up by the acidic sulfinic acid group, while the other is employed in the isomerization. When, however, a 4-fluoroazetidinone wherein R is a butenyl group of the formula B is used, the isomerization is carried out with one molar equivalent or a slight excess thereof.

Illustrative compounds of the invention as represented by the formula 1 include the following:

p-nitrobenzyl 3-methyl-2-(2-oxo-4-fluoro-3-cyanoacetamido-1-azetidinyl)-3-butenoate, p-nitrobenzyl 3-methyl-2-(2-oxo-4-fluoro-3-chloroacetamido-1-azetidinyl)-3-butenoate, diphenylmethyl 3-methyl-2-(2-oxo-4-fluoro-3-acetamido-1-azetidinyl)-3-butenoate, p-methoxybenzyl 3-methyl-2-(2-oxo-4-fluoro-3-p-methoxybenzyloxycarbonylamino-1-azetidinyl)-3-butenoate, p-nitrobenzyl 3-methyl-2-(2-oxo-4-fluoro-3-t-butyloxycarbonylamino-1-azetidinyl)-2-butenoate, p-nitrobenzyl 3-methyl-2-(2-oxo-4-fluoro-3-phthalimido-1-azetidinyl)-3-butenoate, p-nitrobenzyl 3-methyl-2-(2-oxo-4-fluoro-3-succinimido-1-azetidinyl)-2-butenoate, diphenylmethyl 3-methyl-2-(2-oxo-4-fluoro-3-benzamido-1-azetidinyl)-3-butenoate, diphenylmethyl 3-methyl-2-(2-oxo-4-fluoro-3-p-foluamido-1-azetidinyl)-3-butenoate, 3-methyl-2-(2-oxo-4-fluoro-3-p-toluamido-1-azetidinyl)-3-butenoic acid, diphenylmethyl 3-methyl-2-(2-oxo-4-fluoro-3-phenylacetamido-1-azetidinyl)-3-butenoate, diphenylmethyl 3-methyl-2-(2-oxo-4-fluoro-3-phenylacetamido-1-azetidinyl)-2-butenoate, 3-methyl-2-(2-oxo-4-fluoro-3-phenylacetamido-1-azetidinyl)-3-butenoic acid, p-nitrobenzyl 3-methyl-2-(2-oxo-4-fluoro-3-phenoxyacetamido-1-azetidinyl)-3-butenoate p-nitrobenzyl 3-methyl-2-(2-oxo-4-fluoro-3-phenoxyacetamido-1-azetidinyl)-2-butenoate, 3-methyl-2-(2-oxo-4-fluoro-3-phenoxyacetamido-1-azetidinyl)-3-butenoic acid, 2,2,2-trichloroethyl 3-methyl-2-[2-oxo-4-fluoro-3-(2-thienylacetamido)-1-azetidinyl]-3-butenoate, p-nitrobenzyl 3-methyl-2-(2-oxo-4-fluoro-3-phenylmercaptoacetamido-1-azetidinyl)-3-butenoate, 3-methyl-2-(2-oxo-3-fluoro-3-phenylglycylamino-1-azetidinyl)-2-butenoic acid, 3-methyl-2-[2-oxo-4-fluoro-3-(2-hydroxy-2-phenylacetamido)-1-azetidinyl]-2-butenoic acid, and 3-methyl-2-[2-oxo-4-fluoro-3-(2-carboxy-2-phenylacetamido)-1-azetidinyl]-2-butenoic acid.

The compounds of the invention where in formula 1 $R_1$ is an amino group, are prepared by the N-deacylation of a 3-acylamido-4-fluoroazetidinone. The N-deacylation is carried out by the well known two-step N-deacylation process commonly employed in the cephalosporin and penicillin arts for the preparation of the 7-aminocephalosporin nucleus and the 6-aminopenicillin nucleus. According to the method, a 3-acylamido-4-fluoroazetidinone is reacted with an imino halide forming reagent such as phosphorus pentachloride in an inert solvent, for example, a chlorinated hydrocarbon solvent such as methylene chloride, dichloroethane or trichloroethane at a temperature of about −15° C. to about 25° C. to form the corresponding imino chloride. The imino chloride intermediate is converted to the imino ether by treatment of the imino chloride reaction mixture with an alcohol such as methanol or isobutanol. The formation of the imino ether is carried out by first lowering the temperature of the imino chloride reaction mixture to a temperature of about −25° C. followed by addition of at least one molar equivalent of the alcohol. When imino ether formation is complete, the reaction mixture is allowed to warm to room temperature and the imino ether is hydrolyzed by the addition of water to the reaction mixture. The 3-amino-4-fluoroazetidinone of the formula 1 is best recovered from the reaction mixture as the hydrochloride salt. The preparation of the 3-amino compounds of the formula 1 is illustrated by the following reaction scheme.

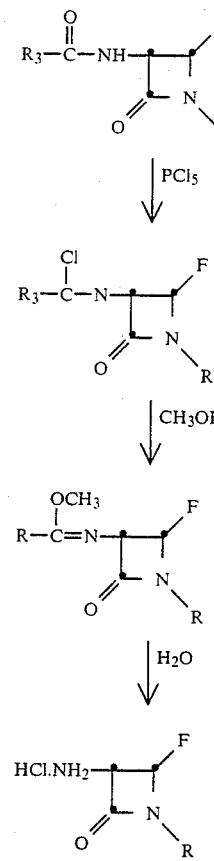

wherein R is

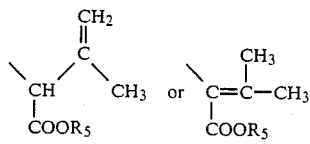

and $R_5$ is a protected carboxy group.

The 3-amino-4-fluoroazetidinones are useful intermediates for the preparation of the 3-acylaminoazetidinones of the formula 1. For example, the 3-amino compounds can be acylated with the desired acyl group to provide a compound of the formula 1 wherein $R_1$ is an acylamido or diacylamino group.

The 3-amino-4-fluoroacetidinones are also obtained by the alternate route comprising the cleavage of a compound of the formula 1 wherein $R_3$ is benzyloxy, p-nitrobenzyloxy, t-butyloxy, 2,2,2-trichloroethoxy, or p-methoxybenzyloxy. These urethane-forming groups are readily removed by known procedures, for example, with a mild acid such as hydrochloric acid or hydrobromic acid. The benzyloxy and substituted benzyloxy groups can be removed also by catalytic hydrogenolysis over palladium on carbon.

The 3-aminoazetidinones of the formula 1 can be obtained as the free amines or as salts formed with mineral acids, for example, hydrochloric acid, hydrobromic acid, sulfuric acid, and phosphoric acid. The salts are formed in a conventional manner, for example, by treating a solution of the free aminoazetidinone in a solvent such as acetone or an alcohol such as ethyl alcohol with an equivalent or a slight excess of the acid. Examples of 3-amino-4-fluoroazetidinones represented by the formula 1 include the following:

p-nitrobenzyl 3-methyl-2-(2-oxo-4-fluoro-3-amino-1-azetidinyl)-3-butenoate,
p-nitrobenzyl 3-methyl-2-(2-oxo-4-fluoro-3-amino-1-azetidinyl)-2-butenoate,
diphenylmethyl 3-methyl-2-(2-oxo-4-fluoro-3-amino-1-azetidinyl)-3-butenoate,
diphenylmethyl 3-methyl-2-(2-oxo-4-fluoro-3-amino-1-azetidinyl)-2-butenoate,
p-methoxybenzyl 3-methyl-2-(2-oxo-4-fluoro-3-amino-1-azetidinyl)-3-butenoate,
t-butyl 3-methyl-2-(2-oxa-4-fluoro-3-amino-1-azetidinyl)-3-butenoate,
2,2,2-trichloroethyl 3-methyl-2-(2-oxo-4-fluoro-3-amino-1-azetidinyl)-2-butenoate,
3-methyl-2-(2-oxo-4-fluoro-3-amino-1-azetidinyl)-3-butenoate,
3-methyl-2-(2-oxo-4-fluoro-3-amino-1-azetidinyl)-2-butenoate, and the acid addition salts thereof formed with mineral acids.

The compounds of the invention represented by the following formula

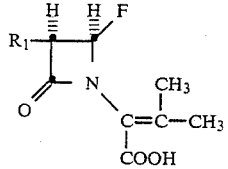

and the pharmaceutically acceptable salts thereof wherein $R_1$ is other than amino, benzyloxycarbonylamino, p-nitrobenzyloxycarbonylamino, t-butyloxycarbonylamino, 2,2,2-trichloroethoxycarbonylamino, or p-methoxybenzyloxycarbonylamino are antibacterial agents which inhibit the growth of microorganisms pathogenic to man and animals. These compounds can be used as topical sterilants and can be formulated at suitable concentrations in liquid form for example, as an aqueous solution or emulsion containing between about 1% and 25% of the active antibacterial agent. The compounds are preferably used in salt form such as the sodium or potassium salt. Other pharmaceutically acceptable salts which can be used include the calcium salt, the aluminum salt, and salts formed with organic amines such as ethanolamine, propanolamine, dibenzylamine, dicyclohexylamine, abietylamine, and like amines.

Preferred compounds represented by the above formula 3 are those wherein $R_1$ is an acylamido group, $R_3$—C(O)NH—. Preferred compounds of this group include those wherein $R_3$ is phenyl or substituted phenyl as defined hereinabove, benzyl, substituted benzyl, phenoxymethyl, and 2-thienyl.

The compounds of the formula 1 wherein $R_5$ is a carboxy-protecting ester group are useful intermediates in the preparation of the above antibacterial compounds. Likewise, the compounds of the formula 1 wherein R is a butenyl group of the above formula B wherein the double bond is in the $\beta,\gamma$-position are intermediates which can be isomerized by the above-described method to the antibacterials of the above formula 3 or to intermediates thereof.

The starting materials employed in the process of this invention, namely, azetidin-2-one-4-sulfinic acids of the above formula 2, are known compounds and are described by Kukolja in U.S. Pat. No. 4,159,266. The azetidinone-4-sulfinic acids are prepared from the corresponding sulfinyl chlorides represented by the following formula

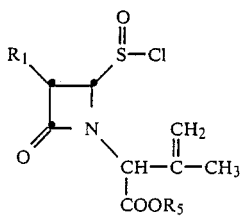

wherein $R_1$ and $R_5$ have the same meanings as defined for formulas 1 and 2 hereinabove. The sulfinyl chloride is dissolved in a suitable water immiscible organic solvent such as ethyl acetate and the solution is slurried with an aqueous solution of sodium bicarbonate. The aqueous layer containing the sulfinic acid sodium salt is separated, washed with ethyl acetate and relayered with fresh ethyl acetate and then acidified. The organic layer containing the sulfinic acid is separated, washed and evaporated to dryness to provide the sulfinic acid as an amorphous solid.

The sodium salts of some of the sulfinic acids used in the invention are sufficiently soluble in ethyl acetate such that only minor amounts will partition into water as described above. In these instances the hydrolysis can be carried out using toluene or alternatively, the azetidinone sulfinyl chloride can be hydrolyzed in an aromatic hydrocarbon such as toluene with 1N hydrochloric acid.

Examples of sulfinic acids useful as starting materials in the process of this invention are the following wherein the formal names are used:

p-nitrobenzyl 3-methyl-2-(2-oxo-4-sulfino-3-phenylacetamido-1-azetidinyl)-3-butenoate,
p-methoxybenzyl 3-methyl-2-(2-oxo-4-sulfino-3-phenoxyacetamido-1-azetidinyl)-3-butenoate,
diphenylmethyl 3-methyl-2-[2-oxo-4-sulfino-3-(4-methylbenzamido)-1-azetidinyl]-3-butenoate,
2,2,2-trichloroethyl 3-methyl-2-(2-oxo-4-sulfino-3-chloroacetamido-1-azetidinyl)-3-butenoate,
p-nitrobenzyl 3-methyl-2-[-2-oxo-4-sulfino-3-(4-nitrobenzyloxycarbonylamino)-1-azetidinyl]-3-butenoate,
2,2,2-trichloroethyl 3-methyl-2-[2-oxo-4-sulfino-3-(2-thienylacetamido)-1-azetidinyl]-3-butenoate,
diphenylmethyl 3-methyl-2-[2-oxo-4-sulfino-3-(2-p-methoxybenzyloxycarbonyl-2-phenylacetamido)-1-azetidinyl]-3-butenoate,
2-iodoethyl 3-methyl-2-(2-oxo-4-sulfino-3-benzamido-1-azetidinyl)-3-butenoate, and
p-methoxybenzyl 3-methyl-2-(2-oxo-4-sulfino-3-phthalimido-1-azetidinyl)-3-butenoate.

The azetidinone sulfinyl chlorides which on hydrolysis form the corresponding sulfinic acids as described above are prepared as described by Kukolja, U.S. Pat. No. 4,081,440.

Examples of 4-chlorosulfinylazetidinones are represented by the following formula

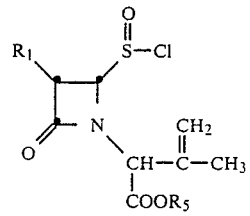

wherein $R_1$ and $R_5$ are as follows:

| $R_1$ | R |
|---|---|
| phenoxyacetamido | p-nitrobenzyl |
| phenoxyacetamido | diphenylmethyl |
| phenoxyacetamido | p-methoxybenzyl |
| phenoxyacetamido | 2,2,2-trichloroethyl |
| phenylacetamido | diphenylmethyl |
| cyanoacetamido | benzyl |
| chloracetamido | t-butyl |
| phthalimido | p-nitrobenzyl |
| succinimido | benzyl |
| 2-thienylacetamido | 2,2,2-trichloroethyl |
| 3-thienylacetamido | 2-iodoethyl |
| 2-furylacetamido | t-butyl |
| benzamido | diphenylmethyl |
| p-methylbenzamido | diphenylmethyl |
| p-chlorobenzamido | diphenylmethyl |
| acetamido | p-nitrobenzyl |
| 2-(p-methoxybenzyloxycarbonyl)-2-phenylacetamido | diphenylmethyl |
| p-chlorophenylthioacetamido | 2,2,2-trichloroethyl |
| p-chlorophenoxyacetamido | p-nitrobenzyl |
| 2-(t-butyloxycarbonylamino)-2-phenylacetamido | diphenylmethyl |
| 2-(tetrahydropyran-2-yl)-2-phenylacetamido | p-nitrobenzyl |
| phenylthioacetamido | p-methoxybenzyl |

As mentioned above the 4-chlorosulfinylazetidinones are known compounds and can be obtained by the method described in U.S. Pat. No. 4,081,440, or as described by Chow in U.S. Pat. No. 4,075,203 using an epoxide or calcium oxide as a non-alkaline acid scavenger. Likewise, Chow describes the use of poly(4-vinylpyridine)-divinylbenzene copolymer crosslinked to about 2% as a preferred acid scavenger in the process for preparing the chlorosulfinylazetidinones with N-chloro halogenating agents, U.S. Pat. No. 4,190,724.

The following examples further illustrate the compounds of the invention and the process for the preparation thereof. In the examples, the following abbreviations are used: pNB=p-nitrobenzyl; pMB=p-methoxybenzyl; DPM=diphenylmethyl.

EXAMPLE 1

Methyl 2-(2-oxo-4-fluoro-3-phenoxyacetamido-1-azetidinyl)-3-butenoic acid

A solution of 2.9 g. (5 mmoles) of p-nitrobenzyl 3-methyl-2-(2-oxo-4-sulfino-3-phenoxyacetamido-1-azetidinyl)-3-butenoate in 100 ml. of methylene chloride was cooled to −78° C. in a dry ice-acetone bath and a solution of 5 mmoles of perchloroyl fluoride in 105 ml. of dry DMF was added by dropwise addition over five minutes. After addition was completed the reaction mixture was stirred in the cold for 20 minutes and was then poured into a mixture of 500 ml. of an aqueous saturated sodium chloride solution and 250 ml. of ethyl acetate. The mixture was shaken, the organic layer separated and washed with aqueous brine and aqueous sodium bicarbonate solution and was dried. The dried solution of the product was evaporated to dryness and the residue of product was mixed with a small volume of ethyl acetate. The product, p-nitrobenzyl 3-methyl-2-(2-oxo-4-fluoro-3-phenoxyacetamido-1-azetidinyl)-3-butenoate, crystallized and was filtered and dried.

IR (CHCl$_3$): 1795 cm$^{-1}$; β-lactam carbonyl.

NMR (CDCl$_3$) δ: 1.87 (s, 3H, CH$_3$), 4.56 (s, 2H, CH$_2$Oφ), 5.01 and 5.18 (m, 2H, CH$_2$=), 5.05 (s, 1H, CHCoopNB), 5.31 (s, 2H, CH$_2$ of pNB), 5.55 (m, 1H, azetidinone H), 5.90 and 6.66 (dd, 1H, azetidinone H), 6.85–8.34 (m, 10H, aromatic H and NH).

To a suspension of 250 mg. of 5% palladium on carbon catalyst in 25 ml. of tetrahydrofuran prehydrogenated on a Parr Hydrogenation apparatus were added a solution of 250 mg. of the 4-fluoroazetidinone prepared as described in the minimum amount of tetrahydrofuran. The suspension was hydrogenated for about 4 hours and was filtered. The filtrate was evaporated under reduced pressure and the residue of product obtained dissolved in ethyl acetate. Water was added to the solution and the pH was adjusted to 7.0. The aqueous phase was separated, layered with fresh ethyl acetate and the pH adjusted to 2.0. The ethyl acetate layer containing the title compound was separated, dried over magnesium sulfate, and evaporated to dryness. The title compound was obtained as a white foam.

EXAMPLE 2

Methyl 2-(2-oxo-4-fluoro-3-phenoxyacetamido-1-azetidinyl)-2-butenoic acid

The 4-fluoroazetidinone ester prepared as described in Example 1 was dissolved in methylene chloride and triethylamine was added with stirring at room temperature. After 30 minutes the isomerization mixture was evaporated to dryness removing the solvent and amine and leaving the isomerizative product, p-nitrobenzyl 3-methyl 2-(2-oxo-4-fluoro-3-phenoxyacetamido-1-azetidinyl)-2-butenoate as residue.

The residue of product was dissolved in THF and the solution added to a suspension of 5% palladium on carbon catalyst in THF. The mixture was hydrogenated as described in Example 1 and the title compound was obtained.

EXAMPLE 3

By following the procedures and conditions described in Example 1, diphenylmethyl 3-methyl-2-(2-oxo-4-fluoro-3-phenylacetamido-1-azetidinyl)-3-butenoate is obtained by reacting the corresponding 4-sufinoazetidinone with perchloroyl fluoride in methylene chloride. The 4-fluoro product is isomerized in methylene chloride with triethylamine and the isomerization product is deesterified with trifluoroacetic acid containing anisole at 5° C. to 3-methyl-2-(2-oxo-4-fluoro-3-phenylacetamido-1-azetidinyl)-2-butenoic acid.

EXAMPLE 4

By following the procedures and conditions described in Example 1, diphenylmethyl 3-methyl-2-(2-oxo-4-fluoro-3-p-toluamido-1-azetidinyl)-3-butenoate is obtained by reacting diphenylmethyl 3-methyl-2-(2-oxo-4-sulfino-3-p-foluamido-1-azetidinyl)-3-butenoate with perchloroyl fluoride.

EXAMPLE 5

2,2,2-Trichloroethyl 3-methyl-2-[2-oxo-4-fluoro-3-(2-thienylacetamido)-1-azetidinyl]-3-butenoate is obtained by reacting 2,2,2-trichloroethyl 3-methyl-2-[2-oxo-4-sulfino-3-(2-thienylacetamido)-1-azetidinyl]-3-butenoate with perchloroyl fluoride under the conditions described in Example 1. The product is isomerized and deesterified to 3-methyl-2-[2-oxo-4-fluoro-3-(2-thienylacetamido)-1-azetidinyl]-2-butenoate.

EXAMPLE 6 p-Methoxybenzyl 3-methyl-2-[2-oxo-4-fluoro-3-(benzyloxycarbonylamino)-1-azetidinyl]-3-butenoate is obtained by reacting the correspondingly substituted azetidinone-4-sulfinic acid with perchloroyl fluoride in 1,1,2-trichloroethane. The product is hydrogenated under 50 psi hydrogen pressure in the presence of 5% palladium on carbon catalyst to produce p-methoxybenzyl 3-methyl-2-(2-oxo-4-fluoro-3-amino-1-azetidinyl)-3-butenoate.

EXAMPLE 7 p-Nitrobenzyl 3-methyl-2-(2-oxo-4-fluoro-3-phthalimido-1-azetidinyl)-3-butenoate is obtained by reacting the correspondingly substituted azetidinone-4-sulfinic acid in chloroform with perchloryl fluoride at −78° C.

EXAMPLE 8 t-Butyl 3-methyl-2-(2-oxo-4-fluoro-3-acetamido-1-azetidinyl)-3-butenoate is obtained by reacting the correspondingly substituted azetidinone-4-sulfinic acid with perchloryl fluoride in methylene chloride at −78° C.

EXAMPLE 9 p-Nitrobenzyl 3-methyl-2-[2-oxo-4-fluoro-3-2-t-butyloxycarbonylamino-2-phenylacetamido)-1-azetidinyl]-3-butenoate is obtained by reacting the correspondingly substituted azetidinone-4-sulfinic acid with perchloryl fluoride in methylene chloride at −78° C. The product is isomerized with triethylamine in methylene chloride to the 2-butenoate and on treatment with trifluoroacetic acid the t-butyloxycarbonyl group is removed. The p-nitrobenzyl ester is next removed by treating the ester with zinc and acetic acid in DMF. There is obtained 3-methyl-2-[2-oxo-4-fluoro-3-(2-amino-2-phenylacetamido)-1-azetidinyl]-2-butenoic acid represented by the formula.

[Structure: phenyl-CH(NH2)-C(O)-NH-[β-lactam with F]-N-C(=C(CH3)CH3)-COOH-...; 4-membered ring bearing F and methyl substituents]

We claim:

1. A process for preparing a 4-fluoroazetidinone of the formula

[Structure: β-lactam ring with R1 and F substituents, N-R]

which comprises mixing in an aprotic inert organic solvent at a temperature between about −80° C. and about −25° C. an azetidinone of the formula

[Structure: β-lactam with R1 and S(=O)-OM substituents, N-R]

with perchloryl fluoride, where in the above formulae R₁ is (1) an imido group of the formula

[Structure: cyclic imide with R2 bridge, two C=O groups, N—]

wherein $R_2$ is $C_2$–$C_4$ alkylene or 1,2-phenylene;

(2) an amido group of the formula $$R_3-\overset{O}{\underset{\|}{C}}-NH-$$

wherein $R_3$ is (a) hydrogen, $C_1$–$C_4$ alkyl, halomethyl, cyanomethyl, benzyloxy, p-nitrobenzyloxy, t-butyloxy, 2,2,2-trichloroethoxy, or p-methoxybenzyloxy;
(b) the group R′, wherein R′ is phenyl or phenyl substituted by 1 or 2 halogens, hydroxy, protected hydroxy, nitro, cyano, $C_1$–$C_4$ alkyl, or $C_1$–$C_4$ alkoxy;
(c) a group of the formula R″—(Q)$_m$—CH$_2$— wherein R″ is R′ as defined above, 1,4-cyclohexadienyl, thienyl or furyl; m is 0 or 1; and Q is O or S; with the limitation that when m is 1, R″ is R′;
(d) a group of the formula

R″—CH—
     |
     W wherein R″ is as defined above, and W is hydroxy, protected hydroxy, carboxy, protected carboxy, amino, or protected amino;
(3) an imidazolidinyl group of the formula

[Structure: imidazolidinone ring with R″-C(=O), N-U, N—, and gem-dimethyl]

wherein R″ is as defined above and U is nitroso or acetyl; or R₁ is
(4) an imido group of the formula

[Structure: R4-C(=O)-N(-)-C(=O)-CH2-(O)n-R′]

wherein R′ is as defined above, n is 0 or 1, and $R_4$ is $C_1$–$C_4$ alkyl, $C_1$–$C_4$ haloalkyl, $C_1$–$C_4$ alkoxy, or 2,2,2-trichloroethoxy;

R is a carboxy-substituted or esterified carboxy-substituted butenyl group represented by the formulas

[Structures: \CH(COOR5)—C(=CH2)—CH3, and \C(COOR5)=C(CH3)—CH3]

wherein $R_5$ is hydrogen or a protected carboxy group; and M is hydrogen, sodium or potassium.

2. The process of claim 1 wherein R is a group of the formula

[Structure: \CH(COOR5)—C(=CH2)—CH3]

3. The process of claim 2 wherein R₁ is an acylamido group $$R_3-\overset{O}{\underset{\|}{C}}-NH-.$$

4. The process of claim 3 wherein R₃ is a group of the formula

R″—(Q)$_m$—CH$_2$—.

5. The process of claim 4 wherein p-nitrobenzyl 3-methyl-2-(2-oxo-4-sulfino-3-phenoxyacetamido-1-azetidinyl)-3-butenoate is mixed with perchloryl fluoride in methylene chloride at a temperature between about −80° C. and about −50° C.

* * * * *